(12) United States Patent
Brotchie

(10) Patent No.: US 6,740,659 B2
(45) Date of Patent: *May 25, 2004

(54) TREATMENT OF DYSKINESIA

(75) Inventor: Jonathan Brotchie, Manchester (GB)

(73) Assignee: Motac Neuroscience Limited, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/210,061

(22) Filed: Aug. 2, 2002

(65) Prior Publication Data
US 2003/0060478 A1 Mar. 27, 2003

Related U.S. Application Data

(63) Continuation of application No. 09/743,965, filed as application No. PCT/GB99/02146 on Jul. 16, 1999, now Pat. No. 6,455,536.

(30) Foreign Application Priority Data

Jul. 18, 1998 (GB) ............................................. 9815618

(51) Int. Cl.⁷ ...................... A61K 31/44; A61K 31/415
(52) U.S. Cl. ...................................... 514/280; 514/399
(58) Field of Search ................................. 514/280, 399

(56) References Cited

FOREIGN PATENT DOCUMENTS

EP 287 339 10/1988
WO WO 92/14364 9/1992

OTHER PUBLICATIONS

CA91:133990, Carroll et al, Psychopharmacology, (Berlin) 1976 64(1) 1–7, abstract.*

MEDLINE AN 93360134, Paakkari et al, J. Pharmacol. Exper. Ther., 1993 Aug. 266 (2) 544–50, abstract.*

DRUG U AN 1996–37422, Brotchi, Drugs Aging, 1996 9 (3) 149–58, abstract.*

National Library of Medicine—Medical Subject Headings, MeSH Descriptor Data; MeSH Tree Structures for dyskinesias, 2003.*

Cadet and Braun, "Naltrexone Inhibits the Persistent Spasmodic Dyskinesia Induced by Chronic Intraperitoneal Administration of Iminodipropionitrile (IDPN)", Neuropeptides 8:87–91 (1986).

MEDLINE 97409757, Pieopponen et al, Pharmacology, Biochemistry and Behaviour 58(1):275–279 (1997)—Abstract.

* cited by examiner

*Primary Examiner*—Rebecca Cook
(74) *Attorney, Agent, or Firm*—Nixon & Vanderhye P.C.

(57) ABSTRACT

The invention relates to the use of compounds which inhibit selectively mu opioid receptor activity, or activation, for the treatment of dyskinesia (which, for example, may arise as a side effect of L-DOPA therapy). The compounds used are preferably mu opioid receptor antagonists such as cyprodime.

10 Claims, 1 Drawing Sheet

TREATMENT OF DYSKINESIA

Figure 1:
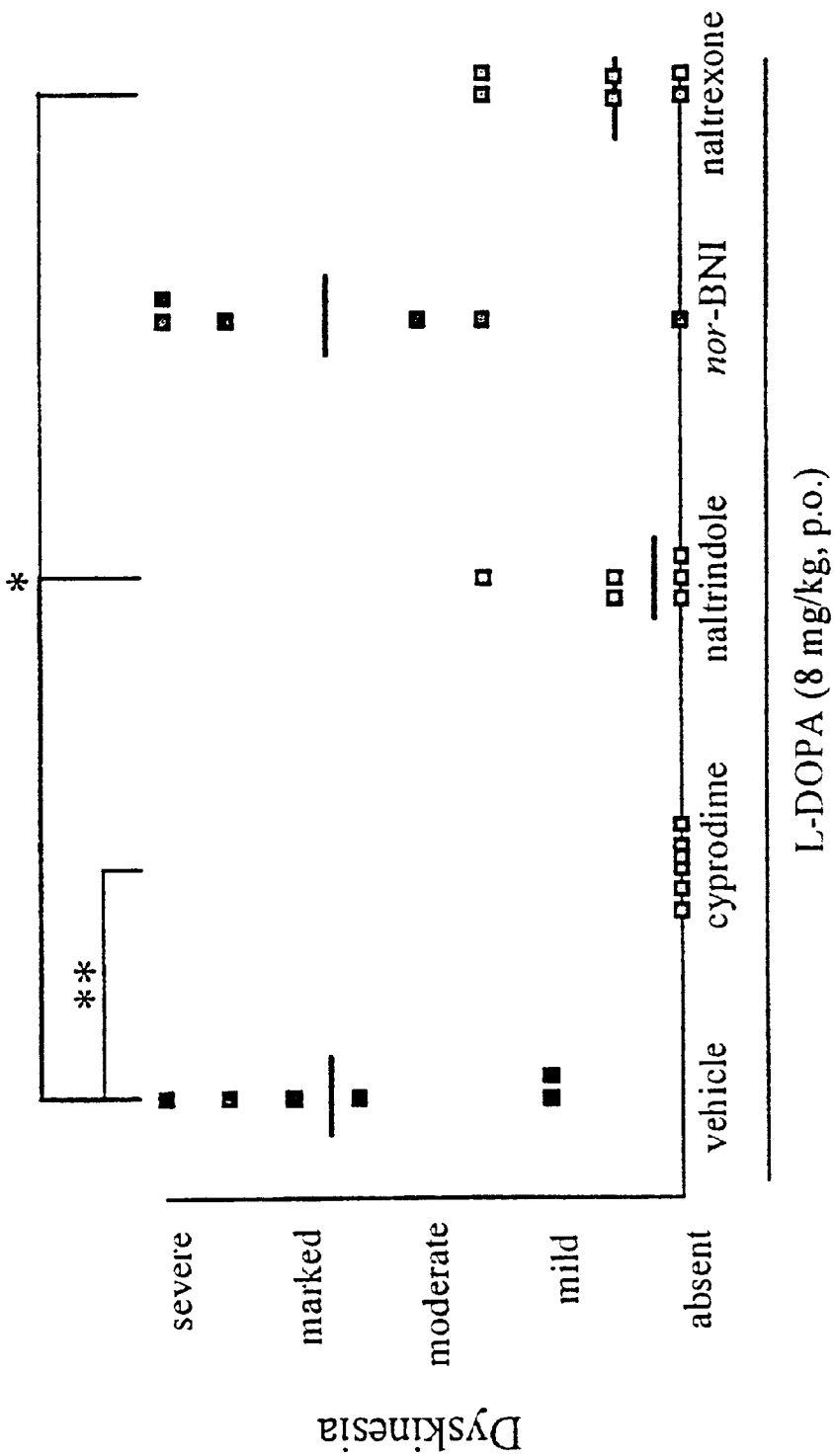

This application is a continuation of application Ser. No. 09/743,965, filed Mar. 20, 2001, now U.S. Pat. No. 6,455,536, which is a 371 of PCT/GB99/02146, filed Jul. 16, 1999, which claims priority from GB 9815618.5, filed Jul. 18, 1998.

The present invention relates to the treatment of dyskinesia.

Dyskinesias are characterised by the development in a subject of abnormal involuntary movements and may manifest as chorea (irregular, involuntary movements of the body, especially the face and extremities) or dystonia (disorder or lack of muscle tonicity).

One way in which dyskinesias may arise is as a side effect of dopamine replacement therapy for Parkinsonism or other basal ganglia-related movement disorders. Parkinsonism is a syndrome of symptoms characterised by slowness of movement (bradykinesia), rigidity and/or tremor. Parkinsonian symptoms are seen in a variety of conditions, most commonly in idiopathic parkinsonism (i.e. Parkinson's Disease) but also following treatment of schizophrenia, manganese poisoning, head injury and the like.

The use of dopamine-replacing agents (e.g. L-DOPA and apomorphine) as symptomatic treatments for conditions such as Parkinson's disease have undoubtedly been successful in increasing the quality of life of patients suffering from the conditions. However, dopamine-replacement therapy does have limitations, especially following long-term treatment. Problems can include a wearing-off of the anti-parkinsonian efficacy of the treatment and in particular the appearance of a range of side effects. These side effects may manifest as dyskinesias such as chorea and dystonia. Dyskinesia can be seen either when the patient is undergoing dopamine-replacement therapy (in the case of chorea and/or dystonia) or even when off therapy (when dystonia is prevalent). Ultimately, these side-effects severely limit the usefulness of dopaminergic treatments.

Many attempts have been made to develop agents which will prevent the development of and/or treat, dyskinesias. For instance, attempts have been made to develop novel dopamine replacement therapies which will obviate or mitigate dyskinetic side effects although such attempts have met with limited success. There is therefore a need to develop ways by which dyskinesias may be treated.

According to a first aspect of the present invention, there is provided a use of a compound which inhibits selectively mu opioid receptor activity, or activation, for the manufacture of a medicament for the treatment of dyskinesia.

According to a second aspect of the present invention, there is provided a composition for use in the treatment of dyskinesia comprising a therapeutically effective amount of a compound which inhibits selectively mu opioid receptor activity, or activation, and a pharmaceutically acceptable vehicle.

According to a third aspect of the present invention, there is provided a method for the treatment of dyskinesia comprising administering to a person or animal in need of such treatment a therapeutically effective amount of a compound which inhibits selectively mu opioid receptor activity or activation.

Mu ($\mu$) opioid receptors are a subclass of opioid receptors which are found in neural tissues and may be activated by endogenous ligands such as endomorphin I and II.

By "selectively" we mean the compound has greater efficacy for inhibiting mu opioid receptor activity or activation than other types of opioid receptor (e.g. delta or kappa opioid receptors).

By "dyskinesia" we mean the development in a subject of abnormal involuntary movements. These movements may manifest as chorea (irregular, involuntary movements of the body, especially the face and extremities) or dystonia (disorder or lack of muscle tonicity). Such movements include ballistic movements and athetoid movements of the trunk, limbs and facial musculature.

The invention is based upon our studies relating to the neural mechanisms underlying L-DOPA-induced dyskinesia. Although we do not wish to be bound by any hypothesis, we believe that dyskinesias (e.g. L-DOPA-induced dyskinesia) is caused by decreased $\gamma$-Aminobutyric acid (GABA) transmission in the lateral segment of the globus pallidus. This transmission is in turn mediated by the activation of D2 dopamine receptors. We believe that compounds which selectively inhibit mu opioid receptor activity or activation may be effective for treating dyskinesias because they regulate this GABA transmission.

We have found that compounds which inhibit selectively mu opioid receptor activity or activation are highly effective for the treatment of dyskinesias. For instance, we have found that dyskinesias (e.g. chorea and dystonia) do not develop, or are at least reduced, when compounds which inhibit mu opioid receptor activity are given to subjects on dopamine-replacement therapy for the treatment of a movement disorder.

We have found that compounds which selectively inhibit mu opioid receptor activity have several advantages over the use of non-selective opioid inhibitors (e.g. naltrexone), or compounds which selectively inhibit the activity of other classes of opioid receptor (e.g. delta or kappa-selective antagonists).

The inventor has established that not only do the compounds used according to the present invention have improved anti-dyskinetic action but they also minimise side effects associated with the blockade of other opioid receptors (e.g. kappa and delta opioid receptors). For instance, a role for kappa opioid receptor mediated transmission has been proposed in the negative regulation of glutamate transmission. Stimulation of kappa opioid receptors thus reduces glutamate release and the blockade of kappa receptors enhances glutamate transmission. Such an action may be associated with an increased pre-disposition towards epilepsy, psychiatric disorders (such as schizophrenia) and neurodegenerative processes (e.g. stroke, Huntington's disease and Alzheimer's disease). Furthermore Delta opioid receptors have been shown to play a role in anti-nociception, thus blockade of endogenous delta opioid transmission my lead to hyperalgesia. The use of selective inhibitors of mu opioid receptors not only results in less dyskinesia but also results in a reduction in the abovementioned side effects of agents which modulate kappa and delta opioid receptors.

Several classes of compound, which may be used according to the invention, are capable of inhibiting mu opioid receptor activity selectively. These compounds include:

(i) mu opioid receptor antagonists or partial agonists which block mu opioid receptors;

(ii) inverse agonists which inverse stimulate mu opioid neural transmission;

(iii) agents which block synthesis of endogenous agonists of mu opioid receptors or which prevent conversion of precursors of mu opioid receptor agonists into their active form;

(iv) agents which inhibit the release of mu opioid receptor agonists:

(v) agents which increase the rate of inactivation of mu opioid receptor agonists; and (vi) agents which block mu opioid receptor expression and/or transcription.

Mu opioid receptor antagonists ((i) above) are preferred inhibitors for use according to the invention. Examples of selective mu opioid receptor antagonists which are suitable for treating dyskinesias include Clocinnamox. Etonitazenyl isothiocyanate, β-funaltrexamine, naloxonazine and cyprodime.

The inventor has found that other, less selective opioid receptor antagonists, such as naloxone or naltrexone (which inhibit mu opioid receptors as well as other types of opioid receptor), have some efficacy for treating dyskinesias but are less effective than compounds used according to the present invention (see the Example).

The compounds (and compositions or medicaments containing them) may be used to treat many types of dyskinesia. For instance the compounds may be used to treat dyskinesia associated with Huntington's disease, idiopathic torsion dystonia, tardive dyskinesia or off-dystonia in Parkinson's disease and most particularly for dyskinesia associated with movement disorders such as parkinsonism (e.g. idiopathic Parkinson's disease, post-encephalitic parkinsonism or parkinsonism resulting from head injury), treatment of schizophrenia, drug intoxication, manganese poisoning and the like.

The compounds are also useful for treatment of dyskinesias which arise as a side-effect of other therapeutic agents. For instance, the compounds are useful for the treatment of dyskinesia associated with ropinirole, pramipexole, cabergoline, bromcriptine, lisuride, pergolide, L-DOPA or apomorphine treatment. The compounds are preferably used for the treatment of dyskinesia associated with L-DOPA or apomorphine treatment.

The compounds are particularly useful for treating dyskinesia caused by agents used to treat movement disorders such as parkinsonism. In this respect a preferred use of the compounds is in the treatment of dyskinetic side-effects associated with L-DOPA or apomorphine therapy for parkinsonism.

The compounds may be used to treat existing dyskinesias but may also be used when prophylactic treatment is considered medically necessary. For instance, when it is considered necessary to initiate L-DOPA therapy and it is feared that dyskinesias may develop.

The compounds may be used to treat dyskinesia as a monotherapy (i.e. use of the compound alone); as an adjunct to medicaments to prevent dyskinetic side-effects caused by the medicament (e.g. as an adjunct to L-DOPA or apomorphine given to treat parkinsonian patients) or alternatively the compounds may be given in combination with other compounds which also reduce dyskinesia.

The compositions of the first and second aspects of the invention may take a number of different forms depending, in particular on the manner in which the composition is to be used. Thus, for example, the composition may be in the form of a powder tablet, capsule, liquid, ointment, cream, gel, hydrogel, aerosol spray, micelle, liposome or any other suitable form that may be administered to a person or animal. It will be appreciated that the vehicle of the composition of the invention should be one which is well tolerated by the subject to whom it is given and enables delivery of the compounds to the brain.

The composition of the invention may be used in a number of ways. For instance, systemic administration may be required in which case the compound may be contained within a composition which may, for example, be ingested orally in the form of a tablet, capsule or liquid. Alternatively the composition may be administered by injection into the blood stream. Injections may be intravenous (bolus or infusion) or subcutaneous (bolus or infusion).

Compounds inhibiting mu opioid receptor activity may also be administered centrally by means of intracerebral, intracerebroventricular, or intrathecal delivery.

The compound may also be incorporated within a slow or delayed release device. Such devices may, for example, be inserted under the skin and the compound which inhibits mu opioid receptor activity may be released over weeks or even months. Such a device may be particularly useful for patients with long term dyskinesia such as patients on continuous L-DOPA therapy for the treatment of Parkinsonism. The devices may be particularly advantageous when a compound is used which would normally require frequent administration (e.g. at least daily ingestion of a tablet or daily injection).

It will be appreciated that the amount of a compound required is determined by biological activity and bioavailability which in turn depends on the mode of administration, the physicochemical properties of the compound employed and whether the compound is being used as a monotherapy or in a combined therapy. The frequency of administration will also be influenced by the above mentioned factors and particularly the half-life of the compound within the subject being treated.

Known procedures, such as those conventionally employed by the pharmaceutical industry (e.g. in vivo experimentation, clinical trials etc), may be used to establish specific formulations of compositions and precise therapeutic regimes (such as daily doses of the compounds and the frequency of administration).

Generally, a daily dose of between 0.01 $\mu$g/kg of body weight and 1.0 g/kg of body weight of a compound which inhibits mu opioid receptor activity may be used for the treatment of dyskinesia depending upon which specific compound is used more preferably the daily dose is between 0.01 mg/kg of body weight and 100 mg/kg of body weight.

Purely by way of example a suitable dose of cyprodime for treating L-DOPA induced dyskinesia in patients with Parkinson's disease is between 0.1 mgs/kg/day and 500 mgs/kg/day (depending upon the health status of the individual). It is preferred that between 0.3 mgs/kg/day and 100 mgs/kg/day of cyprodime is given to a person daily and most preferred that about 10 mgs/kg/day are given (e.g. 8 mgs/kg/day). Cyprodime may be administered by any suitable route including orally.

Daily doses may be given as a single administration (e.g. a daily tablet for oral consumption or as a single daily injection). Alternatively the compound used may require administration twice or more times during a day. As an example, clocinnamox for treating L-DOPA induced dyskinesia in patients with Parkinson's disease may be administered as two (or more depending upon the severity of the dyskinesia) daily doses of between 25 mgs and 5000 mgs in tablet form. A patient receiving treatment may take a first dose upon waking and then a second dose in the evening (if on a two dose regime) or at 3 or 4 hourly intervals thereafter. Alternatively a slow release device may be used to provide optimal doses to a patient without the need to administer repeated doses.

A preferred means of using protein or peptide compounds which inhibit mu opioid receptor activity for the treatment of dyskinesias is to deliver the compound to the brain by means of gene therapy. For instance, gene therapy could be used to decrease expression of mu opioid receptors, increase expression of enzyme(s) which degrade endogenous mu opioid receptor agonists or increase expression of a peptide mu opioid receptor antagonists. Therefore according to a fourth aspect of the present invention there is provided a delivery system for use in a gene therapy technique, said delivery system comprising a DNA molecule encoding for a protein which directly or indirectly inhibits mu opioid receptor activity, said DNA molecule being capable of being transcribed to allow the expression of said protein and thereby treating a dyskinesia.

The delivery systems according to the fourth aspect of the invention are highly suitable for achieving sustained levels of a protein which directly or indirectly inhibits mu opioid receptor activity over a longer period of time than is possible for most conventional delivery systems. The delivery system may be used to induce continuous protein expression from cells in the brain that have been transformed with the DNA molecule. Therefore, even if the protein has a very short half-life as an agent in vivo, therapeutically effective amounts of the protein may be continuously expressed from the treated tissue.

Furthermore, the delivery system of the invention may be used to provide the DNA molecule (and thereby the protein which is an active therapeutic agent) without the need to use conventional pharmaceutical vehicles such as those required in tablets, capsules or liquids.

The delivery system of the present invention is such that the DNA molecule is capable of being expressed (when the delivery system is administered to a patient) to produce a protein which directly or indirectly has activity for modulating mu opioid receptor activity. By "directly" we mean that the product of gene expression per se has the required activity. By "indirectly" we mean that the product of gene expression undergoes or mediates (e.g. as an enzyme) at least one further reaction to provide a compound effective for inhibiting mu opioid receptor activity and thereby treating a dyskinesia.

The DNA molecule may be contained within a suitable vector to form a recombinant vector. The vector may for example be a plasmid, cosmid or phage. Such recombinant vectors are highly useful in the delivery systems of the invention for transforming cells with the DNA molecule.

Recombinant vectors may also include other functional elements. For instance, recombinant vectors can be designed such that the vector will autonomously replicate in the cell. In this case, elements which induce DNA replication may be required in the recombinant vector. Alternatively the recombinant vector may be designed such that the vector and recombinant DNA molecule integrates into the genome of a cell. In this case DNA sequences which favour targeted integration (e.g. by homologous recombination) are desirable. Recombinant vectors may also have DNA coding for genes that may be used as selectable markers in the cloning process.

The recombinant vector may also further comprise a promoter or regulator to control expression of the gene as required.

The DNA molecule may (but not necessarily) be one which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the dyskinesia has been treated or prevented).

The delivery system may provide the DNA molecule to the subject without it being incorporated in a vector. For instance, the DNA molecule may be incorporated within a liposome or virus particle. Alternatively the "naked" DNA molecule may be inserted into a subject's cells by a suitable means e.g. direct endocytotic uptake.

The DNA molecule may be transferred to the cells of a subject to be treated by transfection, infection, microinjection, cell fusion, protoplast fusion or ballistic bombardment. For example, transfer may be by ballistic transfection with coated gold particles, liposomes containing the DNA molecule, viral vectors (e.g. adenovirus) and means of providing direct DNA uptake (e.g. endocytosis) by application of the DNA molecule directly to the brain topically or by injection.

An embodiment of the present invention will now be described, by way of example, with reference to the accompanying drawings, in which:

FIG. 1 is a graph contrasting the effect of vehicle, cyprodime, naltrindole, nor-BNI and naltrexone on dyskinesia.

EXAMPLE

The effect of the selective mu opioid receptor antagonist Cyprodime on dyskinesia was assessed in a 1-methyl-4-phenyl-1,2,3,6-tetrahydropyridine (MPTP)-treated marmoset model of Parkinson's disease.

These effects were contrasted with the effects of the non-selective opioid receptor antagonists naltrexone, the delta opioid selective antagonist naltrindole and the Kappa opioid receptor antagonist nor-BNI.

1. Methods 1.1 Animals used in the study

Six adult common marmosets (*Callithrix jacchus*) were obtained from a closed colony bred at Manchester University, BSU. This study was conducted in the U.K. in accordance with the requirements of The Animals (Scientific Procedures) Act, 1986. The animals were kept in controlled housing conditions, with constant temperature (25° C.), relative humidity (50%) and 12 h light/dark cycles (08.00–20.00 light on). The animals had free access to food (Masuri primate diet-E, Scientific Dietary Services, UK), fresh fruit supplements and water. Marmosets were rendered parkinsonian by treatment with 1-methyl-4-phenyl-1,2,3,6-tetrahydropyridine (MPTP) hydrochloride (Sigma, 2 mg/kg s.c. for 5 consecutive days). This regime has previously been demonstrated to result in a stable parkinsonian syndrome. The animals were allowed to recover for a period of 14 weeks until behavioural assessment was commenced. Stable parkinsonism was defined as when three consecutive assessments of locomotion each one week apart (see below) gave values that did not differ from each other by more than 10%

Dyskinesia was established in these animals by twice daily treatment with L-DOPA (10 mg/kg p.o. as Madopar Dispersible®) for 3 weeks.

1.2 Administration of drugs

Opioid antagonists, or vehicle, were administered with L-DOPA to assess the effects of adjunctive treatment on L-DOPA-induced dyskinesia and the anti-parkinsonian efficacy of L-DOPA. All animals received all treatments. Treatments in any one animal were separated by at least three days. Naltrexone (non-selective antagonist) was administered at a dose of 10 mg/kg (i.p), cyprodime (mu selective antagonist) was administered at a dose of 10 mg/kg (i.p.), naltrindole (delta selective antagonist) was administered at a dose of 10 mg/kg (i.p.), nor-binaltorphimine (nor-BNI, kappa selective antagonist) was administered at a dose of 20 mg/kg (i.p.). Drugs or vehicle were administered with L-DOPA treatment (8 mg/kg p.o.). Behaviour was assessed for 3 hours post drug administration.

1.3 Assessment of behaviour

A battery of behavioural assessments was performed to assess the intensity, range and speed of movements. In addition, postural abnormalities and dyskinesia were assessed.

1) Parkinsonian disability—non-parametric measures based on the following scales
   i) Motor activity (repertoire) score: 0=no movement at all, 1=movement of head or trunk, 2=movement of limbs but no locomotion, on the floor of the cage, 3=on wall of cage/perch, movement of head or trunk, 4=on wall of cage/movement of limbs but no locomotion, 5=walking around/eating on floor of cage, 6=hopping on floor of cage, 7=climbing onto wall of cage or perch, 8=climbing up and down the walls of the cage or along perch, 9=running, jumping, climbing between cage walls/perch/roof, uses limbs through a wide range of motion and activity.
   ii) Bradykinesia score: 0=normal speed of movement, 1=moderate slowing of movement, difficulty initiating and maintaining movement 2=akinetic, unable to move (maximum score in 30 minutes=12).
   iii) Posture score: 0=normal, upright, holds head up, 1=impaired, crouched, face down. (maximum score in 30 minutes=6).

2) Dyskinesia
   0=Absent
   1=Mild, fleeting
   2=Moderate, not interfering with normal activity
   3=Marked, at times interfering with normal activity
   4=Severe, continuous, replacing normal activity Parameters 1 and 2 were assessed every 30 minutes throughout a six hour period by post-hoc analysis of videotape recordings. Assessment was made by an observer blinded to the treatment administered.

1.4 Statistical analysis

Non-parametric measures of mobility, bradykinesia, posture and dyskinesia were cumulated and compared between treatments with a Friedman's test with post hoc Dunn's test where appropriate.

2. Results

FIG. 1 presents the results of the experiments in which dyskinesia in marmosets was assessed following L-DOPA treatment in the MPTP-lesioned marmoset. The data represents cumulative scores for each of the 60 minute assessment periods post-administration. Data are presented as median (horizontal line) and individual values, n=6.

* indicates a significant difference (P=0.05) was observed between the control (vehicle) and naltrindole or naltrexone treated animals.

** indicates a highly significant difference (P=0.01) was observed between the control (vehicle) and cyprodime treated animals.

(i) Marmosets became parkinsonian following treatment with MPTP and when subsequently treated with L-DOPA (8 mg/kg) the parkinsonian symptoms were reversed. Dyskinesia commenced within 5 minutes of L-DOPA administration and was maintained throughout the period of assessment. Dyskinesia scores for animals treated with the vehicle for the opioid antagonists (i.e. controls) are presented in the first column of FIG. 1.

(ii) The second column of FIG. 1 illustrates that median total dyskinesia scores for animals treated with L-DOPA and cyprodime (10 mg/kg) was markedly reduced compared to animals treated with L-DOPA and vehicle for cyprodime only. In fact, each of the cyprodime treated animals exhibited minimal or no dyskinesia.

(iii) Median total dyskinesia scores for animals treated with L-DOPA and the delta opioid antagonist naltrindole (10 mg/kg) are presented in the third column of FIG. 1. Dyskinesia was reduced compared to animals treated with L-DOPA and vehicle for naltrindole only. Although naltrindole treated animals exhibited less dyskinesia it had less efficacy than 10 mg/kg cyprodime because most naltrindole treated animals also had at least some observable dyskinesia.

(iv) Median total dyskinesia scores for animals treated with L-DOPA and the kappa opioid antagonist nor-BNI (20 mg/kg) are presented in the fourth column of FIG. 1. nor-BNI (20 mg/kg) had no effect on L-DOPA-induced dyskinesia.

(v) Median total dyskinesia scores for animals treated with L-DOPA and naltrexone (10 mg/kg) are presented in the fifth column of FIG. 1. Dyskinesia was reduced compared to animals treated with L-DOPA and vehicle for naltrexone only. Although naltrexone treated animals exhibited less dyskinesia it had less efficacy than 10 mg/kg cyprodime because most naltrexone treated animals had at least some observable dyskinesia.

In summary, cyprodime completely abolished dyskinesia in 100% of animals whereas naltrindole and naltrexone only abolished dyskinesia in 50 and 33% of animals respectively. This demonstrates that compounds which inhibits mu opioid receptor activity, or activation, according to the present invention have surprising advantages over non-selective opioid receptor antagonists or kappa and delta opioid receptor selective antagonists.

Although these data demonstrate that inhibitors of mu opioid receptor activity are useful for the treatment of dyskinesia associated with L-DOPA therapy for Parkinson's disease, it will be appreciated that inhibitors of mu opioid receptor activity will be just as useful for treating other types of dyskinesias.

What is claimed is:

1. A method for the treatment of dyskinesia comprising administering to a person or animal in need of said treatment an amount of a compound which inhibits selectively mu opioid receptor activity or activation sufficient to effect said treatment, wherein said dyskinesia is a side effect of a treatment for parkinsonism.

2. The method according to claim 1, wherein the compound is a mu opioid receptor antagonist.

3. The method according to claim 1, wherein said amount is between 0.1 mgs/kg/day and 500 mgs/kg/day.

4. The method according to claim 1, wherein said amount is between 0.3 mgs/kg/day and 100 mgs/kg/day.

5. The method according to claim 1, wherein said amount is about 10 mgs/kg/day.

6. The method according to claim 1 wherein said dyskinesia is a side effect of a treatment for Parkinson's disease.

7. The method according to claim 1 wherein L-DOPA or apomorphine is used in said treatment for parkinsonism.

8. The method according to claim 1, wherein said compound is present in a composition in the form of a powder, tablet, capsule, liquid, ointment, cream, gel, hydrogel, aerosol, spray, micelle, or liposome.

9. The method according to claim 8 wherein the composition is in a form suitable for oral administration.

10. The method according to claim 1 wherein said treatment is prophylactic treatment.

* * * * *